Sept. 27, 1966 E. B. LE GRICE Plant Pat. 2,673
ROSA FLORIBUNDA PLANT
Filed July 15, 1965
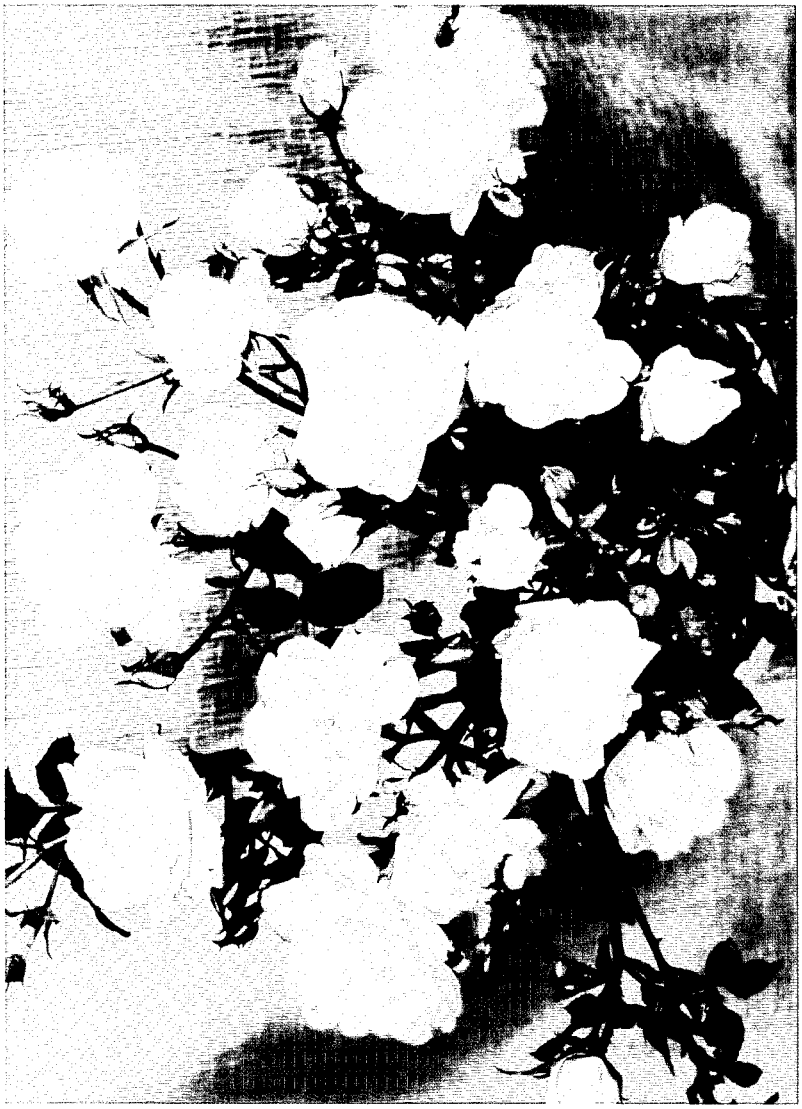
INVENTOR
Edward Burton L. Grice,
BY John S. Thomas,
his ATTORNEY.

United States Patent Office

Plant Pat. 2,673
Patented Sept. 27, 1966

2,673
ROSA FLORIBUNDA PLANT
Edward Burton Le Grice, North Walsham, Norfolk, England
Filed July 15, 1965, Ser. No. 472,375
1 Claim. (Cl. Plt.—24)

This invention relates to a new variety of floribunda rose plant.

The present rose plant was produced originally by the crossing of "Gleaming," an unknown seedling floribunda, as the seed parent, and "Allgold," Plant Pat. No. 1,665, as the pollen parent.

"Gleaming" is a cross of another unknown seedling, and "Allgold."

The new variety was crossed intentionally, in North Walsham, England, in 1961.

The new variety has been asexually reproduced in 1961 at North Walsham, England, by budding.

The drawing shows in color a number of typical stalks with leaves, buds, blooms and thorns.

The roots are average with good winter resistance, when protected, and slight resistance unprotected. It has withstood winter temperatures down to 15° F.

The exposed portion of the plant is in the form of a hardy, perennial, woody bush which is generally upright and symmetrical. A two year old plant grows generally to a height of about 2½ to 3 feet. It is a vigorous grower.

The exposed portion of the plant has good resistance to low temperatures when protected and average resistance when unprotected. Its resistance to drought and wet seasons is good.

For growth, it prefers moderate sun with a south to west exposure. It thrives in well drained, medium loam soil.

The main stalks of the plant are upright, much branched, and stiff. They are adequate to support the foliage and blooms well.

The following color designations are from the British Color Council Horticultural Color Chart and are designated by sheet and number.

The stalks and branches are Spinach Green, No. 0960/3. The color is uniform.

The main stalks range from about 12 to 18 inches in length and are divergent. They have a smooth bark with few thorns. The branches are normal for rose trees. The branches are straight and adequate to support the foliage well.

The foliage in general is open, the leaf arrangement being opposite. The leaves are average in quantity. Both the old and the new leaves are Spinach Green, No. 0960/3, on the top and bottom surfaces. The color is uniform.

The leaves are of medium size, ranging from 3 inches to 4½ inches in length and having a minimum width of about 2 inches and maximum of about 3½ inches. The leaflets are of normal shape, being pinnate with serrated margins, and acute apices. They are of average thickness. They are glossy on the upper face and dull and naked on the reverse. Their persistency on the plant is excellent.

The petioles or leaf stems are Spinach Green, No. 0960/3. They average about 1½ inches in length and are strong. They have a glossy surface texture.

The stipules are slight.

The plant grows and blooms well in all temperate regions. It prefers sun, southern to western exposures, wet seasons, and a well drained, neutral, rich loam soil. The blooms increase in quantity and quality under these optimum growing conditions. Under heat they are smaller and paler.

The plant blooms continuously for a period of about five months. The flowers remain in good condition for a long period when cut.

The buds are usual, being medium in size and plump. They have a glossy aspect and are supported upright on terminals and laterals.

When the sepals first divide, the petal color is Buttercup Yellow, No. 5. When the petals begin to unfurl and when half blown, the color is Buttercup Yellow No. 5.

The sepals are normal in shape and size.

The calyx is of the normal shape and size with a waxy surface texture.

The peduncles average from 1 to 1½ inches in length. They are slightly thorny. Their color is Spinach Green, No. 860/1 shaded to Spinel Red, No. 0023/3. They are strong.

The pedicles average from 1 to 1½ inches in length. Their texture is rough and the color generally is Spinach Green, No. 860/1, shaded with Spinel Red, No. 0023/3. They are strong.

The blooms open at normal rate. They average from 2½ inches in diameter to 3½ inches in diameter, and an average plant will bear about 35 blooms at the same time. The blooms are borne in heads. Each flower lasts about 3 to 4 days on the plant, and 2 to 3 days when cut.

Each bloom has about 25 petals. At the center of the bloom, the petals are Aureolin, No. 3/1. The outer petals are Aureolin, No. 3/2. The base of the petals is Aureolin, No. 3/1. The reverse of the petals is substantially the same color. The blooms are similar in color to "Gleaming."

The general tonality of the plant from a distance, when it is in bloom, is Aureolin, No. 3 to No. 3/1. The color of the flower changes very slightly, if at all, during the blooming season.

The petals are of normal texture. The outer petals are recurvent. The arrangement of the petals is usual. There are from 6 to 10 petaloids in the center. The persistence is good when cut or uncut.

The flower is generally cup shape during opening.

The fragrance of the blooms has a medium lemon perfume. Its lasting quality is good when the blooms are cut or uncut.

The stamens are normal and colored Buttercup Yellow, No. 5/1. The pollen is Buttercup Yellow, No. 5/2.

The styles are about 5 mm. in length and are Aureolin, No. 3/1. The stigmas are about 2 mm. and their color is Crimson, No. 22. The ovaries are plentiful.

The quantity of thorns on the main stalks is moderate and on the laterals few. They are relatively stiff. They are elongated. Their distribution is even on the main stalks and laterals, and uneven on the peduncles. In color they are Spinel Red No. 23/2.

The drawing further illustrates the characteristics of the new variety and the following tabulation is a detailed description of the new variety:

*General*

Parentage:
- *Seed parent.*—Gleaming, unknown seedling. Gleaming, a cross of an unknown seedling and Allgold—Plant Pat. No. 1,665.
- *Pollen parent.*—Allgold.

Classification: Botanic—Rosa floribunda.

Blooming habit: Location where observations were made: North Walsham, England.

Bud:
- *Size.*—Medium.
- *Form.*—Plump.
- *Color.*—When sepals first divide, their color is Buttercup Yellow, No. 5. When they begin to unfurl, they are Buttercup Yellow, No. 5. When half blown, they are Buttercup Yellow, No. 5.

*Sepals.*—Normal shape and size.
*Calyx.*—Normal shape, one inch, with a waxy surface texture.
*Peduncle.*—Strong, length from 1 to 1½ inches.
*Aspect.*—Slightly thorny, Spinach Green, No. 860/1 shaded to Spinel Red, No. 0023/3.
*Pedicles.*—Length—1 to 1½ inches. Texture—rough. Color—Spinach Green, No. 860/1, shaded to Spinel Red, No. 0023/3. Strong.
*Opening.*—Normal.

Bloom:
*Size.*—2½ to 3½ inches in diameter. Average blooms per plant, 35.
*Borne.*—Heads.
*Stems.*—Length—about 12 to 18 inches. Strength—average. Aspect—smooth, with few thorns.
*Form.*—Usual.
*Main stalks.*—Upright and much branched, relatively stiff, divergent from roots, generally adequate to support foliage and bloom.
*Branches.*—Normal for rose trees and relatively straight.
*Permanence.*—3 to 4 days uncut. When cut 2 to 3 days.

Petalage:
*Texture.*—Normal.
*Appearance.*—Normal on the inside and on the outside.
*Form.*—Recurvent.
*Arrangement.*—Unusual.
*Petaloids.*—Few, 6 to 10.
*Persistence.*—Good, when cut and fair to good when uncut.
*Fragrance.*—Medium, lemon like.
*Lasting quality.*—Good when cut or uncut.

Genital organs:
*Stamens.*—Normal and numerous.
*Color.*—Buttercup Yellow, No. 5/1.
*Filaments.*—Medium.
*Pollen.*—Buttercup Yellow, No. 5/2.
*Styles.*—5 mm. Color—Aureolin, No. 3/1.
*Stigmas.*—2 mm. Crimson, No. 22.
*Ovaries.*—Plentiful.

*Plant*

Form: A hardy perennial symmetrical woody, upright, bushy plant.

Growth: Vigorous. Height about 2½ feet to 3 feet for a two year old plant.

Foliage: Opposite arrangement. Open.
*Leaf size.*—Medium, maximum length 3 to 4½ inches, and width of 2 to 3½ inches.
*Quantity.*—Average.
*Color.*—New and old leaves—Spinach Green, No. 0960/3, both top and bottom, color uniform.
*Shape.*—Pinnate with serrated margins and acuminate apices.
*Texture.*—Upper surface—glossy. Lower face—dull and naked.
*Persistency.*—Excellent.
*Leaf characteristics.*—Normal.

Petiole: Length—about 1½ inches. Glossy surface. Strong. Color—Spinach Green, No. 0960/3.

Stipules: Spinach Green, about 1 inch long.

Wood:
*Newest wood.*—Spinach Green, No. 0960/3.
*Bark.*—Smooth.
*Old wood.*—Spinach Green, No. 0960/3.

Thorns:
*Quantity.*—On main stalks—moderate. Laterals—few.
*Form.*—Usual, stiff, elongated, recurvent.
*Color.*—Spinel Red No. 23/2.
*Position.*—Evenly distributed on main stalks and laterals, and unevenly distributed on peduncles.

The plant is characterized particularly by the clarity of color of the blooms, the hybrid tea rose shape of the buds before opening, the strength of growth, flower freedom, and the distinct perfume.

The flower differs from Allgold in having Crimson styles, being somewhat taller with green young and old foliage, and differs from Gleaming in the fullness of flower, being slightly shorter with smaller heads of flowers and more compact in growth.

Having shown and described my new variety of floribunda plant and its manner of asexual reproduction, I claim:

The new and distinct variety of Rosa floribunda plant herein shown and described.

No references cited.

ANTONIO F. GUIDA, *Acting Primary Examiner.*

R. E. BAGWILL, *Assistant Examiner.*